(12) United States Patent
Vollbrecht

(10) Patent No.: US 10,905,595 B2
(45) Date of Patent: Feb. 2, 2021

(54) TEXTILE BANDAGE

(71) Applicant: OTTO BOCK HEALTHCARE GMBH, Duderstadt (DE)

(72) Inventor: Matthias Vollbrecht, Herzberg (DE)

(73) Assignee: OTTOBOCK SE & CO. KGAA, Duderstadt (DE)

( * ) Notice: Subject to any disclaimer, the term of this patent is extended or adjusted under 35 U.S.C. 154(b) by 881 days.

(21) Appl. No.: 15/595,718

(22) Filed: May 15, 2017

(65) Prior Publication Data

US 2017/0246040 A1    Aug. 31, 2017

Related U.S. Application Data

(63) Continuation of application No. 13/696,374, filed as application No. PCT/DE2011/000324 on Mar. 24, 2011, now Pat. No. 9,649,227.

(30) Foreign Application Priority Data

May 7, 2010 (DE) .......................... 10 2010 020 069

(51) Int. Cl.
*A61F 13/06* (2006.01)
*A61F 5/01* (2006.01)
*A61F 13/08* (2006.01)

(52) U.S. Cl.
CPC .......... *A61F 13/061* (2013.01); *A61F 5/0109* (2013.01); *A61F 13/08* (2013.01)

(58) Field of Classification Search
CPC ...... A61F 5/0109; A61F 13/08; A61F 13/061; A61B 11/12; A61B 11/126; A61B 11/128; A41D 2400/80; A41D 2400/82

USPC ....... 602/62–63; 428/85, 89, 91, 92; 28/159, 28/160, 162, 163
See application file for complete search history.

(56) References Cited

U.S. PATENT DOCUMENTS

| 6,149,616 A | 11/2000 | Szlema et al. |
| 9,649,227 B2 * | 5/2017 | Vollbrecht ............ A61F 13/061 |
| 2001/0007929 A1 | 7/2001 | Schlomski |
| 2004/0006295 A1 | 1/2004 | Testa, Jr. et al. |
| 2010/0130903 A1 * | 5/2010 | Rock ...................... D04B 1/246 602/62 |

FOREIGN PATENT DOCUMENTS

| CN | 201199926 Y | 3/2009 |
| DE | 3902434 A1 | 8/1990 |
| DE | 4237389 A1 | 5/1994 |
| DE | 19824649 A1 | 11/1999 |
| DE | 10358146 A1 | 7/2005 |
| DE | 202005015371 U1 | 12/2008 |
| EP | 0229577 B1 | 4/1991 |
| EP | 1114630 A1 | 7/2001 |
| FR | 2591474 A1 | 6/1987 |
| GB | 2241647 A | 9/1991 |
| WO | 2004058117 A1 | 7/2004 |

OTHER PUBLICATIONS

PCT International Search Report for PCT International Patent Application No. PCT/DE2011/000324, dated Jul. 28, 2011.

* cited by examiner

*Primary Examiner* — Kari K Rodriquez
(74) *Attorney, Agent, or Firm* — Holland & Hart, LLP

(57) ABSTRACT

A textile bandage with a bandage body which has an inner face, directed towards a bandage wearer, and an outer face, wherein the surface of the inner face has zones with different marking orientations.

22 Claims, 4 Drawing Sheets

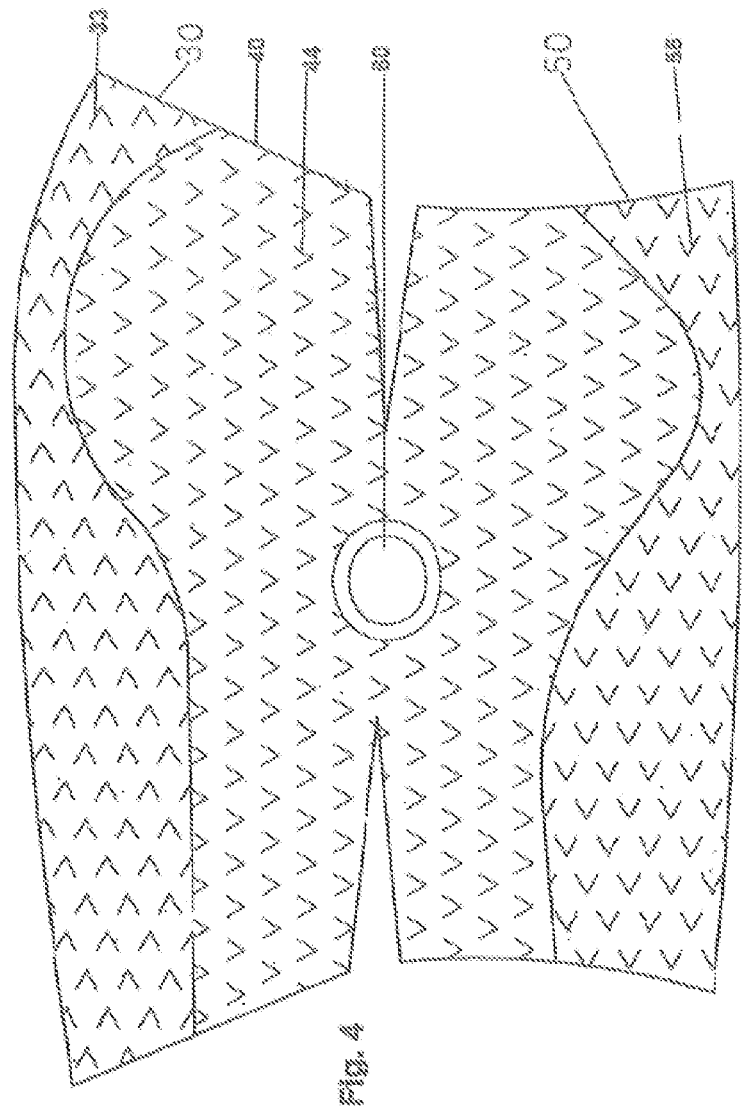

TEXTILE BANDAGE

CROSS-REFERENCE TO RELATED APPLICATION

This is a continuation application of U.S. patent application Ser. No. 13/696,374, filed 6 Nov. 2012, and entitled TEXTILE BANDAGE, issued Mar. 7, 2013 as U.S. Pat. No. 9,649,227, which is a U.S. National Entry application from PCT International Patent Application No. PCT/DE2011/000324, filed 24 Mar. 2011, and also entitled TEXTILE BANDAGE, which claimed the benefit of German Patent Application No. 102010020069.7, filed 7 May 2010, the disclosures of which are incorporated, in their entireties, by this reference.

TECHNICAL FIELD

The invention relates to a textile bandage with a bandage body which has an inner face, directed toward a bandage wearer, and an outer face.

BACKGROUND

Textile bandages are generally hose-shaped textile products that are pulled over limbs or the trunk and bear on the location for which they are intended. Textile bandages are often worn in the area of joints in order to support or protect these, for example in knee or elbow guards in sport or in ankle bandages that are intended to have a protective and supporting action. Moreover, bandages are known that are arranged around muscle groups in order to exert a heating function and a compression function in addition to a protective function. To make them easier to pull on and to adapt them to the different dimensions of the respective limbs, the textile bandages are provided with an elastic bandage body which ensures that, after the bandage has been widened, it bears tightly on the intended location without disturbing the blood flow.

While a bandage is being worn, the movement of the limbs or of the trunk causes a relative movement between the bandage and the limb, such that bandages often shift out of position. This is generally compensated by the bandage wearer repositioning the bandages. If the bandage has shifted, the intended function of protection or support cannot be fully performed.

SUMMARY

The object of the present invention is to make available a textile bandage that has improved properties in terms of avoiding the bandage shifting.

According to the invention, this object is achieved by a textile bandage having the features of the main claim. Advantageous embodiments and refinements of the invention are disclosed in the dependent claims, in the description and in the figures.

In the textile bandage according to the invention, with a bandage body which has an inner face, directed toward a bandage wearer, and an outer face, provision is made that the surface of the inner face has zones with different nap orientations. Surfaces with a nap have the property whereby the resistances against a shearing load are different depending on the direction of movement. Similarly to a scale arrangement that provides a high or low degree of flow resistance depending on the direction of flow, it is also the case in textiles, fibers or also pelts that the resistance is effected by an orientation of the fibers, hairs, threads or the like. Other configurations of a nap orientation can likewise be provided, for example a layered structure of folds, material overlaps or the like. This is designated as nap orientation. An arrangement of zones with different nap orientations has the effect that the textile bandage, during the movement, has no preferred direction of shifting, and instead the anti-shift properties arise in different directions. In this way, resistances against shifting are made available in multiple orientations, such that the textile bandage remains in the intended position on the bandage wearer, even in the event of loads with different directions of the relative movement.

In the respective zones, the nap orientation can be configured uniformly, such that relatively large surface areas are equipped with the same nap orientation. It is thereby possible to produce a textile bandage at relatively low cost. However, provision can also be made that no zones of large surface area are provided in the bandage, and instead only individual small areas with different nap orientations are arranged on the inner face of the bandage. Different nap orientations can therefore adjoin each other directly or can be present alongside each other and spatially separate from each other.

It is not necessary that the zones with different nap orientations are formed over the entire surface. Similarly, areas without a nap can be provided, for example if areas of the textile bandage need to have a different configuration in order to provide special functions or to receive functional elements. Areas without a nap can, for example, have particular elasticities in order to adapt the textile bandage to the particular purpose.

At least one zone of the textile bandage can have a nap orientation directed against a rotation movement, such that the positional stability of the applied textile bandage is ensured. The direction of rotation of the bandage depends on the individual muscle structure, the muscle tone and other anatomical circumstances. For a course of therapy or for an improved function, it may be necessary and important that the textile bandage does not rotate or shift out of position. Therefore, for example, an upper zone of the textile bandage can have a nap orientation directed against a medial rotation. The upper zone is regarded as that area of a textile bandage that is oriented proximally when a textile bandage is applied. In order to avoid a rotation movement of the textile bandage on the body, the nap orientation is oriented against a medial rotation, such that an increased resistance to rotation in this direction is present. A lower zone, that is to say a distally oriented zone, can have a nap orientation directed against a lateral rotation, that is to say a rotation to the outside. In particular, a combination of a nap orientation against a medial rotation and a nap orientation against a lateral rotation, which are arranged in different zones, results in a contra-directional resistance orientation and cancels out the tendency toward rotation, such that the textile bandage has less tendency to shift out of position. Provision can also be made that the upper zone is oriented against a lateral rotation and the lower zone against a medial rotation. An orientation against rotation about the longitudinal extent is also possible in the middle area of the textile bandage.

At least one further zone can be present that has a nap orientation directed only against downward shifting. On account of the generally conical configuration of the limbs, which narrow in the direction of the joints, there is a basic tendency for textile bandages to shift downward or become compressed in the area of the joints. A nap orientation directed against downward shifting or upward shifting counteracts this tendency.

In addition to an orientation directed against rotation or against upward shifting or downward shifting, it is also possible for nap orientations to be present by which superposed movement components are counteracted. For example, a nap orientation that is mainly directed against a medial or lateral rotation can also have a component against downward shifting. This can be achieved by the nap orientation being turned about a certain angle relative to the preferred direction. In this way, shifting in the circumferential direction and downward shifting are equally prevented, in which case the resistances against shifting in the respective direction vary depending on the angle of the nap orientation.

Functional elements can be arranged on the bandage body, for example for the fixing or orientation of guides. The functional elements can serve as a patella guide or for stabilizing the bandage body as a whole. Through the arrangement of functional elements, the bandage can be designed as an orthosis, which performs a supporting function. Parts of the orthosis rail or the orthosis rails themselves can be secured on the bandage body itself in order to ensure an assignment of the functional elements to the respective limbs. For secure fixing, it is possible for tensioning elements to be secured on the bandage body or functional elements, for example belts or straps, which are secured by buckles or velcro fasteners.

The bandage body is preferably elastic and can be formed from a woven fabric or a knit.

The textile bandage is preferably designed as a knee-joint bandage with a recess or cutout in the area of the patella, so as to ensure that minimal pressure is applied to the patella during the movement. It is likewise possible, in an embodiment of the textile bandage as an elbow bandage, to form a recess or cutout in the area of the elbow.

To provide for the nap orientations, nap velour can be arranged on the inner face of the bandage body, which nap velour is arranged across the entire surface of the inner face or in parts that are spaced apart from one another.

BRIEF DESCRIPTION OF THE DRAWINGS

Illustrative embodiments of the invention are explained in more detail below with reference to the attached figures, in which:

FIG. 4 shows a blank for the bandage according to FIG. 3.

DETAILED DESCRIPTION

Figure 1:
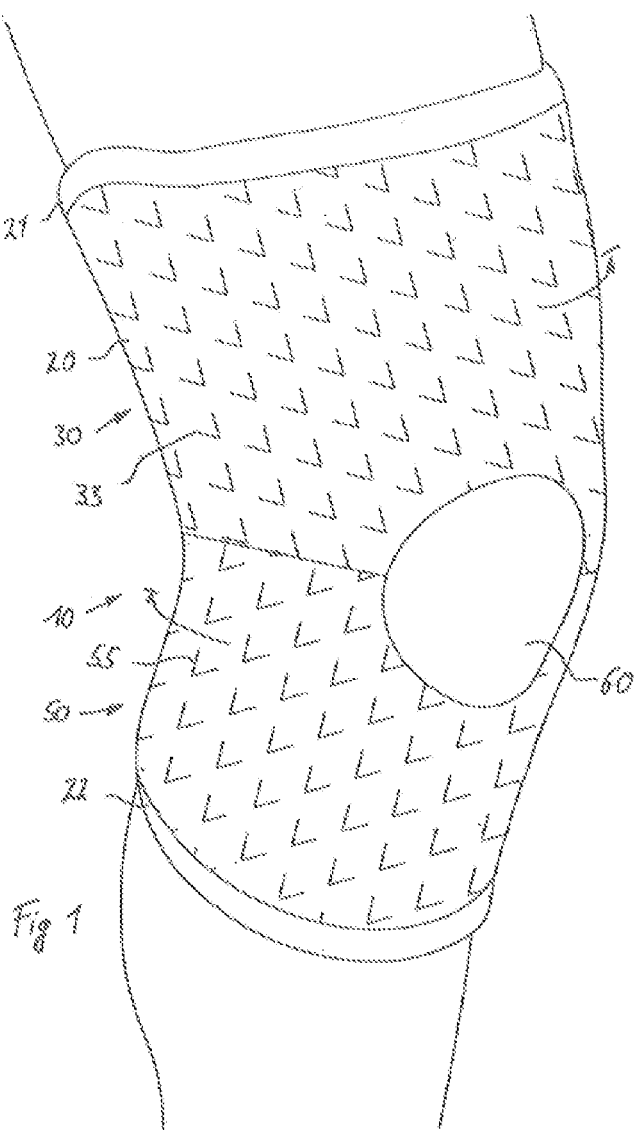
FIG. 1 shows a view of a fitted knee bandage.

A textile bandage 10 in the form of a knee bandage is shown in FIG. 1. The knee bandage 10 has a bandage body 20, which has a hose-shaped design. An upper closure cord 21 is arranged at its proximal end, and a lower closure cord 22 is arranged at its distal end. The bandage body 20 is elastic, like the closure cords 21, 22, and can be designed as a woven or knitted fabric. A recess 60 is formed in the area of the patella in order to ensure that, while the textile bandage 10 is being worn, the patella is not subjected to too great a pressure.

In the illustrative embodiment shown, the bandage body 20 is divided into two zones 30, 50, a first zone 30 extending above the knee joint space and a second zone 50 extending below the knee joint space, such that an upper or proximal zone 30 and a lower or distal zone 50 are formed. On the inner face of the bandage body 20, elements with a structure are applied which have different nap orientations 33, 55. The different nap orientations 33, 55 on the surface of the inner face of the bandage body 20 are illustrated by the respectively differently oriented patterns, wherein the nap orientation extends from the open side of the triangle to the vertex, such that a movement from the vertex to the open side encounters greater resistance than the reverse movement.

It will be seen from FIG. 1 that the nap orientation 33 of the upper zone 30 is substantially the opposite of the nap orientation 55 of the lower zone. While the nap orientation 33 counteracts a medial rotation, the nap orientation 55 of the lower zone 50 counteracts a lateral rotation, as is indicated by the respective arrows.

Figure 2:
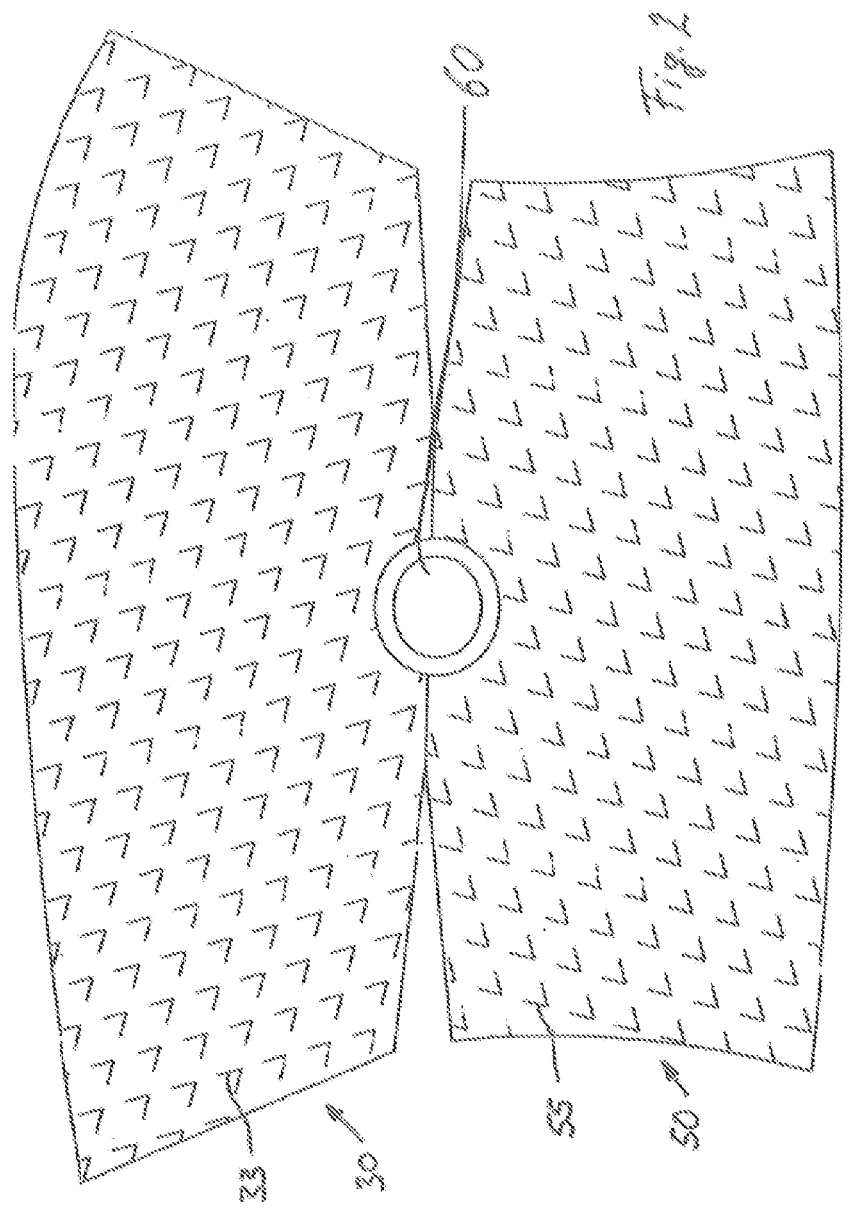
FIG. 2 shows a blank for a knee bandage according to FIG. 1.

A blank for a textile bandage is shown in a plan view in FIG. 2 in the state before being sewn together. The recess 60 for the patella is arranged centrally, and the zones 30, 50 are entirely coated with a corresponding material, such that mutually opposite nap orientations 33, 55 are present. As an alternative to the embodiment shown with complete coating or coverage of the surface of the inner face of the blank, it is also possible for only individual areas of the zones 30, 50 to be provided with materials that have a nap, such that areas without a nap alternate with areas having a nap. Different nap orientations can also occur within the zones 30, 50, such that improved fixing of the applied textile bandage is achieved.

Figure 3:
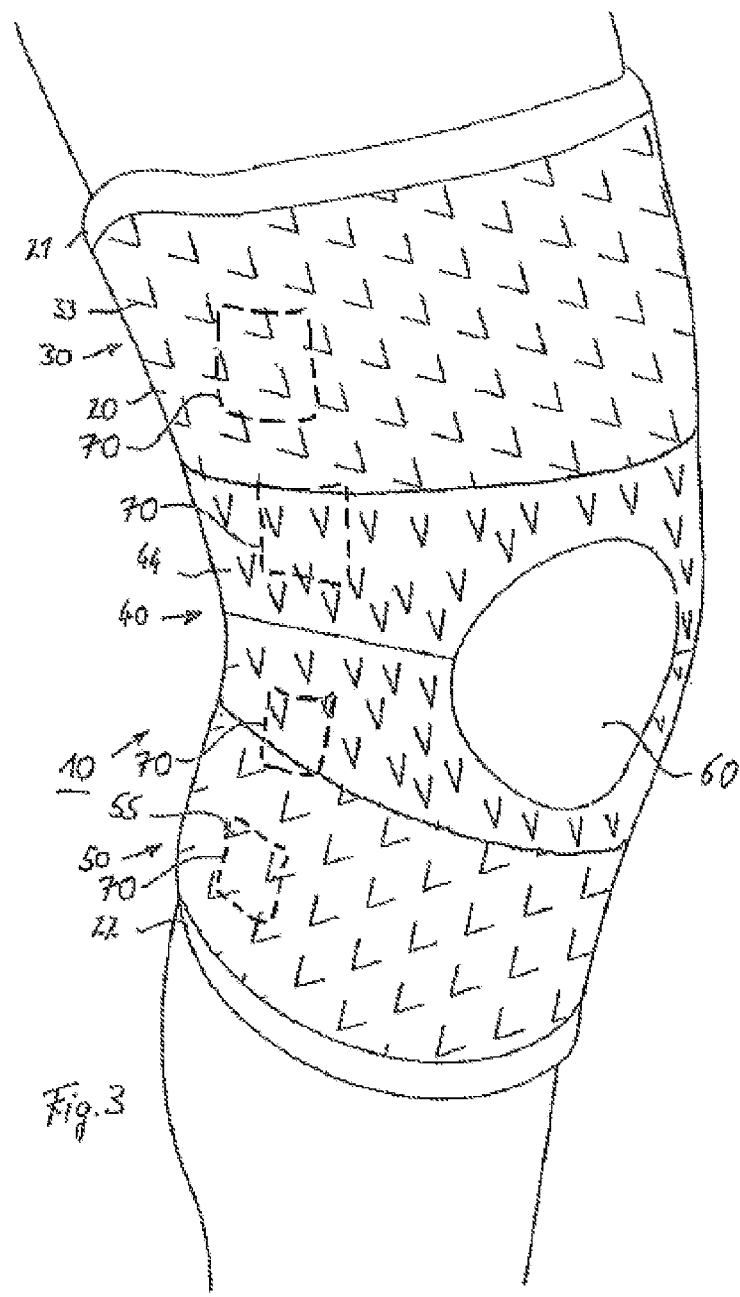
FIG. 3 shows a variant of FIG. 1.

A variant of the invention is shown in FIG. 3, in which the textile bandage 10 as a whole has three zones 30, 40, 50, wherein the upper zone 30 has a nap orientation 33 which is oriented at approximately 45° with respect to the perpendicular and is oriented against rotation and downward shifting, the central zone 40, which is formed in the area of the patella, has a nap orientation which is oriented only against downward shifting, and the lower zone 50 has a nap orientation 55 which again is offset by 45° with respect to the perpendicular and prevents or reduces downward shifting and rotation. The nap orientations 33, 55 of the upper zone 30 and lower zone 50 are differently oriented, for example counter to each other, although it is also possible in principle that these orientations 33, 55 are also oriented such that they act partially against shifting, for example an upward shifting of the lower zone or a downward shifting of the upper zone 30, and against rotation or only against rotation.

A possible blank for a textile bandage with three zones 30, 40, 50 is shown in FIG. 4. The individual zones 30, 40, 50 are provided with curved boundaries, such that areas of different sizes with corresponding nap orientations 33, 44, 55 are present at different locations of the textile bandage 10. It is thus possible to ensure that those areas exposed to a high degree of twisting or shearing load have a particularly high degree of rotation resistance by virtue of a suitably large surface area with suitably designed nap orientations.

The nap orientations 33, 44, 55 can be obtained, for example, by a nap velour or another surface configuration. It is important that different shear resistances are made available depending on the direction of movement, such that a high degree of resistance is provided in one direction and less resistance is provided in the opposite direction. The nap orientations of the upper zone 30 and lower zone 50 are counter to each other and directed against rotation, while the middle zone 40 provides an orientation parallel to the perpendicular, which acts against shifting in the longitudinal direction of the limb or of the textile bandage.

The nap orientations 33, 55 in the upper zone 30 and lower zone 50 can be designed in opposite directions in order to avoid rotation, such that function elements 70, which can be arranged on the textile bandage 10, remain in position. The blank according to FIG. 4 is suitable for a knee bandage, since the upper zone 30 is wider than the lower zone 50 and is thus adapted to the anatomical circumstances of the knee with thigh and lower leg.

The invention claimed is:

1. A textile bandage, comprising:
a bandage body which has an inner face adapted to be directed toward a bandage wearer, an outer face, a plurality of first nap structures, and a plurality of second nap structures, the plurality of first nap structures and the plurality of second nap structures providing different resistances against a shearing load depending on a direction of shifting of the textile bandage relative to the bandage wearer;
wherein a surface of the inner face has a plurality of zones, a first of the plurality of the zones including the first nap structures, each nap structure in the first of the plurality of zones being oriented at a first angle relative to the inner face to limit shifting of the textile bandage relative to the bandage wearer in at least a first direction, and a second of the plurality of zones including the second nap structures, each nap structure in the second of the plurality of zones being oriented at a second angle relative to the inner face to limit shifting of the textile bandage relative to the bandage wearer in at least a second direction, the first and second angles being different from each other when measured in a common plane and the first and second nap structures are viewed in a common direction.

2. The textile bandage as claimed in claim 1, wherein the nap structures of each zone are configured uniformly.

3. The textile bandage as claimed in claim 1, wherein areas without nap structures are formed in the plurality of zones.

4. The textile bandage as claimed in claim 1, wherein at least one of the first nap structures or second nap structures is directed against a rotation movement.

5. The textile bandage as claimed in claim 4, wherein the nap structures directed against rotation have an orientation component against downward shifting or upward shifting.

6. The textile bandage as claimed in claim 1, wherein at least one of the first nap structures or second nap structures is directed against downward shifting or upward shifting.

7. The textile bandage as claimed in claim 1, wherein functional elements are arranged on the bandage body.

8. The textile bandage as claimed in claim 1, wherein the bandage body is elastic.

9. The textile bandage as claimed in claim 1, wherein the textile bandage is formed as a knee-joint bandage with a recess or cutout adapted to fit an area of a patella of the bandage wearer or as an elbow bandage with a recess or cutout adapted to fit an area of an elbow of the bandage wearer.

10. The textile bandage as claimed in claim 1, wherein at least one of the first and second nap structures includes nap velour arranged on the inner face of the bandage body.

11. A textile bandage, comprising:
a bandage body comprising:
an inner face directed toward a skin surface of a bandage wearer, the inner surface having at least first and second zones;
an outer face directed away from the skin surface;
a plurality of first nap structures formed on the inner face in the first zone to limit shifting of the textile bandage relative to the skin surface in at least a first direction;
a plurality of second nap structures formed on the inner face in the second zone to limit shifting of the textile bandage relative to the skin surface in at least a second direction;
wherein the plurality of first nap structures and the plurality of second nap structures provide different resistances against a shearing load depending on a direction of shifting of the textile bandage relative to the bandage wearer;
wherein each of the nap structures in the first zone is oriented at a first angle relative to the inner face, and each of the nap structures in the second zone is oriented at a second angle relative to the inner face that is different from the first angle when the first and second angles are measured in a common plane and the first and second nap structures are viewed in a common direction.

12. The textile bandage as claimed in claim 11, wherein the nap structures of each of the first and second zones are configured uniformly.

13. The textile bandage as claimed in claim 11, wherein areas without nap structures are formed in the first and second zones.

14. The textile bandage as claimed in claim 11, wherein at least one of the first nap structures or second nap structures is directed against a rotation movement of the textile bandage.

15. The textile bandage as claimed in claim 14, wherein the nap structures directed against a rotation movement have an orientation component against downward shifting or upward shifting.

16. The textile bandage as claimed in claim 11, wherein at least one of the first nap structures or second nap structures is directed against downward shifting or upward shifting.

17. The textile bandage as claimed in claim 11, further comprising functional elements arranged on the bandage body.

18. The textile bandage as claimed in claim 11, wherein the bandage body is elastic.

19. The textile bandage as claimed in claim 11, wherein the textile bandage is formed as a knee-joint bandage with a recess or cutout in an area of a patella of the bandage wearer or as an elbow bandage with a recess or cutout in an area of an elbow of the bandage wearer.

20. The textile bandage as claimed in claim 11, wherein at least one of the first and second nap structures includes nap velour arranged on the inner face of the bandage body.

21. A textile bandage, comprising:
a bandage body which has an inner face adapted to be directed toward a bandage wearer, an outer face, a plurality of first nap structures, and a plurality of second nap structures, the plurality of first nap structures and the plurality of second nap structures providing different resistances against a shearing load depending on a direction of shifting of the textile bandage relative to the bandage wearer;
wherein a surface of the inner face has a plurality of zones, a first of the plurality of the zones including the first nap structures, each nap structure in the first of the plurality of zones being oriented at a first angle relative to the inner face to limit shifting of the textile bandage relative to the bandage wearer in at least a first direction, and a second of the plurality of zones including the second nap structures, each nap structure in the second of the plurality of zones being oriented at a second angle relative to the inner face to limit shifting of the textile bandage relative to the bandage wearer in at least a second direction, the first and second angles being different from each other when measured in a common plane and the first and second nap structures are viewed in a common direction;

wherein at least one of the first nap structures or second nap structures is directed against a rotation movement.

22. A textile bandage, comprising:

a bandage body which has an inner face adapted to be directed toward a bandage wearer, an outer face, a plurality of first nap structures, and a plurality of second nap structures, the plurality of first nap structures and the plurality of second nap structures providing different resistances against a shearing load depending on a direction of shifting of the textile bandage relative to the bandage wearer;

wherein a surface of the inner face has a plurality of zones, a first of the plurality of the zones including the first nap structures, each nap structure in the first of the plurality of zones being oriented at a first angle relative to the inner face to limit shifting of the textile bandage relative to the bandage wearer in at least a first direction, and a second of the plurality of zones including the second nap structures, each nap structure in the second of the plurality of zones being oriented at a second angle relative to the inner face to limit shifting of the textile bandage relative to the bandage wearer in at least a second direction, the first and second angles being different from each other when measured in a common plane and the first and second nap structures are viewed in a common direction;

wherein at least one of the first nap structures or second nap structures is directed against downward shifting or upward shifting.

* * * * *